US012746358B2

(12) United States Patent
Wang et al.

(10) Patent No.: US 12,746,358 B2
(45) Date of Patent: Sep. 29, 2026

(54) MASK, SAMPLE COLLECTING TUBE, AND PATHOGEN COLLECTING APPARATUS

(71) Applicant: MGI TECH CO., LTD., Shenzhen (CN)

(72) Inventors: Jian Wang, Shenzhen (CN); Jianghu Wu, Shenzhen (CN); Qing Xie, Shenzhen (CN); Haoyan Kuang, Shenzhen (CN); Chunyu Geng, Shenzhen (CN); Shuo Huang, Shenzhen (CN)

(73) Assignee: MGI Tech Co., Ltd., Shenzhen (CN)

( * ) Notice: Subject to any disclaimer, the term of this patent is extended or adjusted under 35 U.S.C. 154(b) by 821 days.

(21) Appl. No.: 18/184,482

(22) Filed: Mar. 15, 2023

(65) Prior Publication Data

US 2023/0218847 A1 Jul. 13, 2023

Related U.S. Application Data

(63) Continuation of application No. PCT/CN2020/119384, filed on Sep. 30, 2020.

(51) Int. Cl.

| | |
|---|---|
| ***A61M 16/06*** | (2006.01) |
| ***A61M 16/08*** | (2006.01) |
| ***A61M 16/10*** | (2006.01) |
| ***A61M 16/20*** | (2006.01) |

(52) U.S. Cl.

CPC .......... *A61M 16/06* (2013.01); *A61M 16/085* (2014.02); *A61M 16/1055* (2013.01); *A61M 16/1065* (2014.02); *A61M 16/208* (2013.01)

(58) Field of Classification Search

CPC ................ A61M 16/06; A61M 16/085; A61M 16/1055; A61M 16/1065; A61M 16/208; A61M 16/0683; A41D 31/02; A41D 31/04; A41D 31/30; A41D 13/11–1192;

(Continued)

(56) References Cited

U.S. PATENT DOCUMENTS

| | | | | |
|---|---|---|---|---|
| 2011/0290256 A1* | 12/2011 | Sather ................. | A61M 16/208 128/207.18 |
| 2018/0071729 A1* | 3/2018 | Peltosaari ............ | B65D 41/185 |
| 2020/0061399 A1* | 2/2020 | Wade ................... | A62B 18/025 |

FOREIGN PATENT DOCUMENTS

| | | |
|---|---|---|
| CN | 103656902 A | 3/2014 |
| CN | 107249745 A | 10/2017 |
| CN | 210445776 U | 5/2020 |

(Continued)

OTHER PUBLICATIONS

Machine Translation of CN111513377A Description Accessed Jan. 7, 2026 (Year: 2026).*

(Continued)

*Primary Examiner* — Elliot S Ruddie

(74) *Attorney, Agent, or Firm* — Lee & Hayes, P.C.

(57) ABSTRACT

Provided are a mask, a sample collecting tube, and a pathogen collecting apparatus. The mask includes a mask body, a breather valve fixed on the mask body, and a sampling structure including a pathogen adsorption portion. The pathogen adsorption portion is disposed on an inner side of the breather valve and is adapted to adsorb pathogens in exhaled gas. The pathogen adsorption portion is adapted to enter the sample collecting tube to be in contact with a sample preservation solution in the sample collecting tube.

16 Claims, 9 Drawing Sheets

(58) Field of Classification Search
CPC ............ A62B 7/00–14; A62B 9/02–06; B01D 46/00–90; B01D 47/00
See application file for complete search history.

(56) References Cited

FOREIGN PATENT DOCUMENTS

| | | | | | |
|---|---|---|---|---|---|
| CN | 111227347 A | | 6/2020 | | |
| CN | 111264937 A | | 6/2020 | | |
| CN | 111505076 A | | 8/2020 | | |
| CN | 111513377 A | * | 8/2020 | ............. | A41D 31/04 |
| FR | 2709066 A1 | | 2/1995 | | |
| IN | 111513377 A | | 8/2020 | | |

OTHER PUBLICATIONS

International Search Report and Written Opinion mailed Jun. 23, 2021 in International Application No. PCT/CN2020/119384, 16 pages.

* cited by examiner

MASK, SAMPLE COLLECTING TUBE, AND PATHOGEN COLLECTING APPARATUS

CROSS-REFERENCE TO RELATED APPLICATIONS

The present application is a continuation of International Application No. PCT/CN2020/119384, filed on Sep. 30, 2020, which is incorporated here by reference in its entirety.

FIELD

The present disclosure relates to the technical filed of medical supplies, and in particular, to a mask, a sample collecting tube, and a pathogen collecting apparatus.

BACKGROUND

The coronavirus disease 2019 (COVID-19) is mainly propagated through respiratory droplets, close contact, aerosols formed by respiratory droplets, and the like. Related detections such as nucleic acid detection and antibody detection are performed by collecting viruses exhaled by a patient. At present, the sample is collected mainly through a throat swab and a nose swab. Such a collecting method not only brings discomfort to a person sampled, but also requires training on sampling techniques and procedures for a sampling person. The sampling person also needs to be specially protected to avoid infection. As a whole, these collecting methods have high operational risks, high sampling costs, and low efficiency.

SUMMARY

The present disclosure aims to solve at least one of the technical problems in the related art.

To this end, a first objective of the present disclosure is to provide a mask, with which the collection work of aerosol particles that may contain viruses can be completed while comfort of a wearer is ensured, and a risk of a collector being infected can be effectively avoided in a sampling process.

A second objective of the present disclosure is to provide a sample collecting tube, with which a pathogen adsorption portion in the mask may be removed.

A third objective of the present disclosure is to provide a pathogen collecting apparatus, with which the pathogen adsorption portion in the mask may be collected for further detection and assay.

For achieving the above objectives, a first aspect of the present disclosure provides a mask. The mask includes: a mask body; a breather valve fixed on the mask body; and a sampling structure including a pathogen adsorption portion. The pathogen adsorption portion is disposed on an inner side of the breather valve and is adapted to adsorb pathogens in exhaled gas, and the pathogen adsorption portion is adapted to enter a sample collecting tube to be in contact with a sample preservation solution in the sample collecting tube.

By disposing the pathogen adsorption portion in the breather valve in the mask of the present disclosure, it is possible to complete collection of aerosol particles exhaled by a wearer while the comfort of the wearer is ensured, which avoids various discomfort of the wearer in a sampling process, effectively avoids a risk of the sampling person being infected in the sampling process and a pollution risk of a sample, enables simultaneous sampling of multiple persons, and greatly improves sampling efficiency.

Further, the breather valve is a one-way valve and is configured to be opened when a wearer exhales and to be closed when the wearer inhales.

Further, the breather valve includes: a valve casing having an exhaust vent; and a valve plate disposed on the valve casing and configured to expose the exhaust vent when the wearer exhales and to close the exhaust vent when the wearer inhales.

Further, the pathogen adsorption portion is disposed on an inner side of the exhaust vent.

Further, one end of the valve plate is disposed on the valve casing, and another end of the valve plate is optionally pressed tight on the valve casing to open or close the exhaust vent.

Further, a plurality of exhaust vents is provided, and the plurality of exhaust vents is arranged at intervals in a circumferential direction of the valve casing. The valve plate is formed in an annular shape, an inner end of the valve plate is fixedly connected to the valve casing, and an outer end of the valve plate is optionally pressed tight on the valve casing to expose or close the plurality of exhaust vents.

Further, the valve plate has a plurality of micropores. The plurality of micropores is configured to: when the wearer exhales, become larger in pore diameter and be in communication with the exhaust vent; and when the wearer inhales, become smaller in the pore diameter until the plurality of micropores is closed.

Further, the valve casing is detachably disposed on the mask body.

Further, the valve casing is in threaded fit with the mask body.

Further, the valve casing is connected to the pathogen adsorption portion.

Further, the breather valve further includes a valve cover. The valve cover is arranged on an outer side of the valve casing, and an exhaust space is defined by the valve cover and the valve casing; and the valve cover has an air vent in communication with the exhaust space.

Further, a blocking cover that optionally seals the air vent is disposed on the valve cover. Further, the valve cover is detachably connected to the valve casing.

Further, the valve cover is in threaded fit with the valve casing.

Further, the valve cover is connected to the pathogen adsorption portion.

Further, the valve plate is disposed in the exhaust space. The valve plate has a filter layer disposed on an outer side thereof.

Further, the filter layer has a fluffy state in which the filter layer is adapted to filter incoming air from the air vent, and a compressed state in which the filter layer is air-tight and water-impermeable.

Further, the mask further includes a tightening apparatus connected to the filter layer and adapted to compress the filter layer and seal the air vent when the tightening apparatus is tightened.

Further, a waterproof sheet is disposed outside the filter layer. The waterproof sheet is optionally pressed tight on the valve cover to seal the air vent.

Further, the breather valve is detachably mounted on the mask body.

Further, the breather valve is optionally mounted on the sample collecting tube to seal an inlet of the sample collecting tube.

Further, the breather valve is optionally in threaded fit with the mask body or the sample collecting tube.

Further, the mask body has a base disposed thereon, and the breather valve is detachably mounted on the base.

Further, after the breather valve is detached from the mask body, the pathogen adsorption portion is adapted to move away from the breather valve under an action of an external force to be in contact with the sample preservation solution.

Further, after the breather valve is detached from the mask body, the pathogen adsorption portion is adapted to detach from the breather valve under the action of the external force to be in contact with the sample preservation solution.

Further, the sampling structure further includes a fixation frame, and the pathogen adsorption portion is disposed on the fixation frame.

Further, the pathogen adsorption portion is disposed on an inner end of the fixation frame. An outer end of the fixation frame is disposed inside the breather valve. A part of the breather valve directly facing the outer end of the fixation frame is formed as an elastic region which, when stressed, deforms and pushes the fixation frame.

Further, the pathogen adsorption portion is disposed on an inner end of the fixation frame. An outer end of the fixation frame extends beyond an outer side of the breather valve to form a pressing portion.

Further, the fixation frame includes an inner fixation frame and an outer fixation frame that are separated from each other. The inner fixation frame is connected to the breather valve and is adapted to detach from the breather valve under the action of the external force, the pathogen adsorption portion is disposed on an inner end of the inner fixation frame, an outer end of the outer fixation frame extends beyond an outer side of the breather valve to form a pressing portion, and an inner end of the outer fixation frame optionally abuts against an outer end of the inner fixation frame.

Further, the breather valve has a mounting hole, and at least part of the inner fixation frame passes through the mounting hole and is in interference fit with the mounting hole.

Further, a weak connection portion is disposed between the inner fixation frame and the breather valve. The weak connection portion is adapted to be broken under the action of the external force to detach the inner fixation frame from the breather valve.

Further, the breather valve has a limiting portion disposed thereon. After the outer fixation frame pushes the inner fixation frame to detach from the breather valve, the limiting portion is adapted to restrict the outer fixation frame from moving towards the inner fixation frame.

Further, each of the inner fixation frame and the outer fixation frame is formed as a rod-shaped structure. The limiting portion includes a limiting block disposed on the outer fixation frame and a limiting groove that is disposed on the breather valve and in snap fit with the limiting portion. A diameter of the limiting portion is greater than a diameter of the inner fixation frame.

Further, the inner end of the fixation frame has a supporting disk disposed thereon, the supporting disk has a first via hole, and the pathogen adsorption portion is disposed on the supporting disk and covers the first via hole.

Further, the inner end of the fixation frame has a supporting cylinder disposed thereon, an inner end of the supporting cylinder is opened, a cylinder wall of the supporting cylinder has a second via hole, and the pathogen adsorption portion is disposed on the supporting cylinder and covers the second via hole.

Further, the base is formed as a cylindrical structure, and the base has an air inlet hole in a bottom thereof. The pathogen adsorption portion is adapted to block the air inlet hole.

Further, an inner end of the fixation frame is disposed on the breather valve or the base. The pathogen adsorption portion is disposed on an outer end of the fixation frame.

Further, the fixation frame is formed as a fixation cylinder, an outer end of the fixation cylinder is opened, and an inner end of the fixation cylinder has a third via hole; and the pathogen adsorption portion is disposed at the inner end of the fixation cylinder and covers the third via hole.

Further, the fixation cylinder is detachably disposed on the breather valve or the base.

Further, the fixation cylinder is snapped and fixed to the breather valve or the base.

Further, the fixation cylinder has a pulling portion disposed thereon.

Further, the fixation cylinder includes a fixation cylinder body and a bottom wall portion disposed at an outer end of the fixation cylinder body. The bottom wall portion has the third via hole, and the bottom wall portion is configured to detach from the fixation cylinder body under the action of the external force.

Further, the bottom wall portion is detachably disposed on the fixation cylinder body.

Further, the bottom wall portion is snapped and fixed to the fixation cylinder body.

Further, the breather valve has an exhaust channel disposed therein. At least part of the sampling structure is disposed in the exhaust channel.

Further, the pathogen adsorption portion is disposed on an inner end of the fixation frame. An outer end of the fixation frame is connected to the breather valve. At least part of the fixation frame is adapted to be inserted into the sample collecting tube and is adapted to be broken off under the action of the external force.

Further, the fixation frame has a strength weakened region configured to be broken under the action of the external force.

Further, the fixation frame is formed as a cylindrical structure, and an outer diameter of the fixation frame is smaller than an inner diameter of the sample collecting tube.

Further, the pathogen adsorption portion is disposed on an inner end of the fixation frame. An outer end of the fixation frame is connected to the breather valve. The pathogen adsorption portion is adapted to be cut by a cutting portion on the sample collecting tube to detach from the fixation frame.

Further, the sampling structure further includes: a limiting member disposed on the valve body; a plurality of mounting support feet; and a force bearing rod. An inner end of each of the plurality of mounting support feet is connected to an outer periphery of the pathogen adsorption portion. An outer end of the force bearing rod is formed as a force bearing end, and an inner end of the force bearing rod optionally applies a force towards the plurality of mounting support feet or the pathogen adsorption portion to deform the pathogen adsorption portion.

Further, an outer end of each of the plurality of mounting support feet is hinged to the limiting member. The force bearing rod is adapted to push and deform the pathogen adsorption portion.

Further, an outer end of each of the plurality of mounting support feet is connected to an inner end of the force bearing rod. The force bearing rod is adapted to pull the outer end of each of the mounting support feet to enable the plurality of mounting support feet to be gathered up under pushing of the limiting member and to deform the pathogen adsorption portion.

Further, the limiting member is formed as an annular limiting ring.

Further, the pathogen adsorption portion is connected to the fixation frame through a water-soluble material layer.

A second aspect of the present disclosure provides a sample collecting tube. The sample collecting tube includes: a collecting tube body having an opening and a sample collecting solution disposed inside; and a cover body detachably disposed on the collecting tube body to close or expose the opening. The collecting tube body has a cutting portion disposed therein, and the cutting portion is adapted to cut the pathogen adsorption portion.

Further, the cutting portion is disposed on an inner peripheral wall of the collecting tube body.

Further, the cutting portion is disposed adjacent to the opening.

Further, a plurality of cutting portions is provided. The plurality of cutting portions is arranged at intervals in a circumferential direction of the collecting tube body.

A third aspect of the present disclosure provides a pathogen collecting apparatus. The pathogen collecting apparatus includes: a sample collecting tube having a sample preservation solution disposed therein; and the mask described above. The pathogen adsorption portion on the mask is adapted to enter the sample collecting tube to be in contact with the sample preservation solution in the sample collecting tube.

Additional aspects and advantages of the present disclosure will be given at least in part in the following description, or become apparent at least in part from the following description, or can be learned from practicing of the present disclosure.

BRIEF DESCRIPTION OF THE DRAWINGS

The above and/or additional aspects and advantages of the present disclosure will become more apparent and more understandable from the following description of embodiments taken in conjunction with the accompanying drawings, in which.

Figure 1:
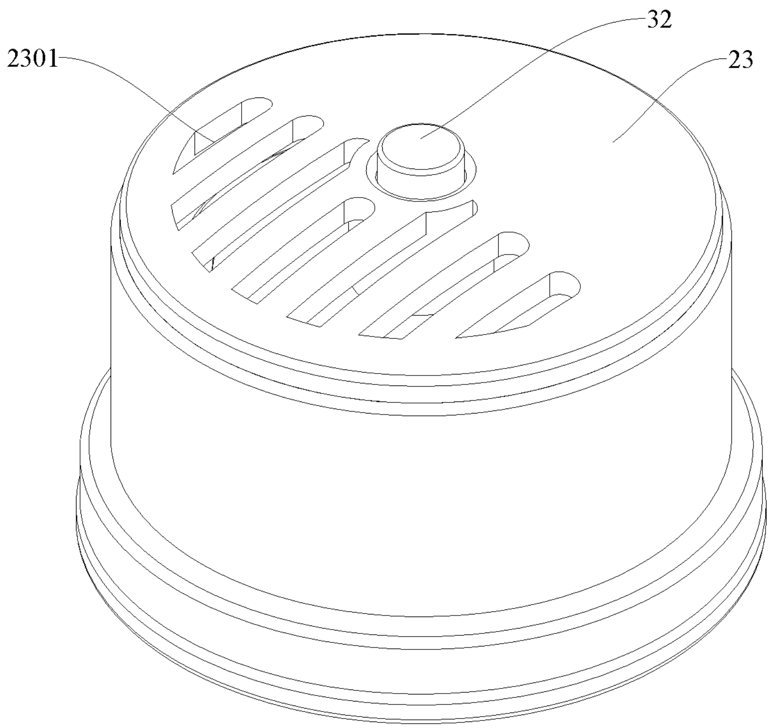
FIG. 1 is a schematic structural diagram of a mask according to an embodiment of the present disclosure.

REFERENCE NUMERALS mask 1000,
mask body 1,
breather valve 2, valve casing 21, valve plate 22, valve cover 23,
pathogen adsorption portion 31,
fixation frame 32, inner fixation frame 321, outer fixation frame 322, pulling portion 323,
limiting member 33, mounting support foot 34, force bearing rod 35,
base 4,
sample collecting tube 2000,
collecting tube body 2001, cover body 2002, cutting portion 2003, preservation solution 2004.

DETAILED DESCRIPTION

The embodiments of the present disclosure will be described in detail below with reference to examples thereof as illustrated in the accompanying drawings, throughout which same or similar elements or elements having same or similar functions are denoted by same or similar reference numerals. The embodiments described below with reference to the drawings are illustrative, and are only intended to explain rather than limit the present disclosure.

A mask 1000 according to the embodiments of the present disclosure will be described below with reference to FIG. 1 to FIG. 16. The mask 1000 includes: a mask body 1, a breather valve 2 fixed on the mask body 1, and a sampling structure including a pathogen adsorption portion 31. The pathogen adsorption portion 31 is disposed on an inner side of the breather valve 2 and is adapted to adsorb pathogens in exhaled gas. The pathogen adsorption portion 31 is adapted to enter a sample collecting tube 2000 to be in contact with a sample preservation solution 2004 in the sample collecting tube 2000.

At present, samples are collected mainly through a throat swab and a nose swab. Such collecting methods not only bring discomfort to persons sampled, but also require training on sampling techniques and procedures for sampling persons. The sampling persons also need to be specially protected to avoid infection. As a whole, these collecting methods have high operational risks, high sampling costs, and low efficiency.

In view of the defects existing in the current collecting methods, the present disclosure envisages the use of the mask 1000. The pathogen adsorption portion 31 is disposed on the mask 1000 to collect viruses, which can reduce the discomfort of the person sampled by replacing a manner of collecting the sample through the throat swab or the nose swab. However, if the pathogen adsorption portion 31 was directly adhered to an inner surface of the mask 1000, on one hand, a thickness of the mask body 1 would be increased to increase a stuffy feeling during wearing; and on the other hand, the pathogen adsorption portion 31 would be required to be cut or folded into a predetermined size before being immersed in the preservation solution for storage, which not only is tedious to operate, but also increases a risk of infection due to excessive contact between a sampling person and the pathogen adsorption portion 31 during sampling and a transfer process of the pathogen adsorption portion 31. At the same time, the sample also has a pollution risk, which may affect accuracy of a detection result.

Based on the above considerations, in order to add the pathogen adsorption portion 31 without increasing the thickness of the mask body 1 and to facilitate the removal of the pathogen adsorption portion 31, according to the present disclosure, the breather valve 2 is disposed on the mask 1000, and the pathogen adsorption portion 31 is placed inside the breather valve 2. In this way, during the sampling, it is only required that the pathogen adsorption portion 31 is removed and then placed into the sample collecting tube 2000, or the pathogen adsorption portion 31 is directly moved into the sample collecting tube 2000, and the sampling person does not need to directly contact the pathogen adsorption portion 31, which reduces a risk in operation of the sampling person and ensures safety of the sampling person.

Since the present disclosure can directly collect viruses in exhaled gas of a wearer by using the mask 1000, there is no need for the collection operation of the sampling person. Therefore, there is no need for the training on sampling techniques and procedures. With the mask 1000 of the present disclosure, it is possible to implement simultaneous sample collection of multiple wearers, and save manpower while improving sample collection efficiency.

In order to ensure accuracy of collecting the pathogen adsorption portion 31 and avoid an influence of viruses in outside air on the sample, in the present disclosure, the pathogen adsorption portion 31 is disposed on the inner side of the breather valve 2, i.e., at a side close to the wearer. Therefore, the pathogens in the exhaled gas can be directly sampled after the wearer breathes, which prevents the viruses in the outside air from affecting the sample and causing a test result to be inaccurate and unnecessary economic, manpower and other losses for medical apparatus and instruments, medical staff, and a person who provides the sample.

With the mask 1000 of the present disclosure, by disposing the pathogen adsorption portion 31 in the breather valve 2, it is possible to complete collection of aerosol particles exhaled by the wearer while ensuring comfort of the wearer, which avoids various discomfort of the wearer in a sampling process, effectively avoids a risk of the sampling person being infected in the sampling process and a pollution risk of the sample, enables to implement simultaneous sampling of multiple persons, and greatly improves sampling efficiency.

According to an embodiment of the present disclosure, the breather valve 2 is a one-way valve and is configured to be opened when a wearer exhales and to be closed when the wearer inhales.

In order to ensure accuracy of the sample and prevent the viruses in the outside air from affecting the sample, the breather valve 2 of the present disclosure is a one-way valve. When the wearer exhales, the breather valve 2 is opened to collect the viruses in the exhaled gas of the wearer to the pathogen adsorption portion 31. When the wearer inhales, the breather valve 2 is closed to prevent air from entering the pathogen adsorption portion 31 from the breather valve 2 to damage the sample and affect accuracy of the result.

According to an embodiment of the present disclosure, the breather valve 2 includes a valve casing 21 and a valve plate 22.

In some embodiments, the valve casing 21 has an exhaust vent. The valve plate 22 is disposed on the valve casing 21 and configured to expose the exhaust vent when the wearer exhales and to close the exhaust vent when the wearer inhales.

The valve casing 21 is fixed on the mask body 1. The gas exhaled by the wearer may be discharged through the exhaust vent on the valve casing 21. The valve plate 22 is disposed at a position of the exhaust vent for opening or closing the exhaust vent, which is specifically embodied as: opening the exhaust vent when the wearer exhales, and closing the exhaust vent when the wearer inhales.

According to an embodiment of the present disclosure, the pathogen adsorption portion 31 is disposed on an inner side of the exhaust vent.

It should be noted that "inner" in the present disclosure can be understood as a direction close to a face side of the wearer, and "outer" can be understood as a direction away from the face side of the wearer. The exhaust vent opens when the wearer exhales and closes when the wearer inhales. It can be considered that the pathogen adsorption portion 31 only collects the viruses in the exhaled gas of the wearer when being disposed at a side close to the wearer. If the pathogen adsorption portion 31 is disposed on an outer side of the exhaust vent, the pathogen adsorption portion 31 is exposed in the air, and whether the sample is only viruses exhaled by the wearer cannot be determined.

According to an embodiment of the present disclosure, one end of the valve plate 22 is disposed on the valve casing 21, and another end of the valve plate 22 is optionally pressed tight on the valve casing 21 to expose or close the exhaust vent. When the wearer exhales, the valve plate 22 is activated, and the exhaust vent is in an open state. When the wearer inhales, the valve plate 22 is pressed tight on the casing, and the exhaust vent is in a closed state.

According to an embodiment of the present disclosure, a plurality of exhaust vents is provided. The plurality of exhaust vents is arranged at intervals in a circumferential direction of the valve casing 21. The valve plate 22 is formed in an annular shape. An inner end of the valve plate 22 is fixedly connected to the valve casing 21, and an outer end of the valve plate 22 is optionally pressed tight on the valve casing 21 to expose or close the plurality of exhaust vents. The valve plate 22 may be a solid part. When the wearer exhales, the valve plate 22 is screwed out or opened to achieve activation. When the wearer inhales, the valve plate 22 is screwed back or pressed tight on the casing to achieve closing.

According to an embodiment of the present disclosure, the valve plate 22 has a plurality of micropores. The micropore is configured to become larger in pore diameter and be in communication with the exhaust vent when the wearer exhales, and is configured to become smaller in the pore diameter until the micropore is closed when the wearer inhales. The valve plate 22 may be a chemical material. When the wearer exhales, the pore diameter of the micropore on the valve plate 22 becomes larger and the micropore is in communication with the exhaust vent. When the wearer inhales, the pore diameter of the micropore on the valve plate 22 becomes smaller until the exhaust vent is closed.

According to an embodiment of the present disclosure, the valve casing 21 is detachably disposed on the mask body 1. Since the pathogen adsorption portion 31 is disposed on the inner side of the breather valve 2, the pathogen adsorption portion 31 is required to be taken out to be tested when the sample is collected, the valve casing 21, as a part of the breather valve 2, may be detached from the mask body 1, and then the pathogen adsorption portion 31 is processed in a next step.

In some embodiments, the valve casing 21 is in threaded fit with the mask body 1. The valve casing 21 may be separated from the mask body 1 by rotating, and then the pathogen adsorption portion 31 is processed in the next step.

According to an embodiment of the present disclosure, the valve casing 21 is connected to the pathogen adsorption portion 31.

According to an embodiment of the present disclosure, the breather valve 2 further includes a valve cover 23. The valve cover 23 is arranged on an outer side of the valve casing 21, and an exhaust space is defined by the valve cover 23 and the valve casing 21. The valve cover 23 has an air vent in communication with the exhaust space. The gas exhaled by the wearer is discharged from the exhaust vent, and then discharged from the air vent to the outside environment through the exhaust space.

According to an embodiment of the present disclosure, a blocking cover that optionally seals the air vent is disposed on the valve cover 23.

In an actual sampling process, it is difficult to ensure that an outside environment is a sterile environment. In order to ensure the accuracy of the detection result, all viruses collected in the pathogen adsorption portion 31 are expected to be those exhaled by the wearer. From a perspective of improving applicability of the mask 1000 to various detection environments and the accuracy of the detection result, the blocking cover is further disposed on the valve cover 23 to enable the air vent to be sealed or opened, and the exhaust space is isolated from the outside air by using the blocking cover, which effectively prevents viruses possibly existing in the outside air from entering the exhaust space and improving accuracy and reliability of a final detection result.

In some embodiments, the blocking cover may be formed as a rotary blocking cover. One end of the blocking cover is disposed on the valve cover 23, and another end of the blocking cover is optionally pressed tight on the blocking cover to expose or close the air vent. The blocking cover may also be a material, which closes the air vent by being pulled through a pulling rope.

It should be noted that a form of the blocking cover is not limited to the above examples and is within the scope of the present disclosure provided that an objective of sealing and opening the air vent in the valve cover 23 can be achieved.

According to an embodiment of the present disclosure, the valve cover 23 is detachably connected to the valve casing 21. Since the pathogen adsorption portion 31 is arranged on the inner side of the breather valve 2, the pathogen adsorption part 31 is required to be taken out to be tested when the sample is collected, and after the valve cover 23 is detached from the valve casing 21, the valve casing 21 and the pathogen adsorption portion 31 are left, and it is then more convenient to process the pathogen adsorption portion 31

According to an embodiment of the present disclosure, the valve cover 23 is in threaded fit with the valve casing 21. The valve cover 23 is separated from the valve casing 21 by rotating the valve cover 23.

According to an embodiment of the present disclosure, the valve cover 23 is connected to the pathogen adsorption portion 31.

According to an embodiment of the present disclosure, the valve plate 22 is disposed in the exhaust space. The valve plate 22 has a filter layer disposed on an outer side thereof.

On one hand, in order to ensure the accuracy of the detection result, all the viruses collected in the pathogen adsorption portion 31 are expected to be those exhaled by the wearer. On the other hand, in order to prevent the sample preservation solution 2004 from leaking out of the sample collecting tube 2000 to pollute a surrounding environment in a sample test process, in the present disclosure, the filter layer is disposed on the outer side of the valve plate 22, i.e., the filter layer is disposed in the exhaust space. The filter layer has a good sealing effect and a good filtering effect, which on one hand, may prevent viruses in the outside environment from polluting the pathogen adsorption portion 31, and on the other hand, may close the sample collecting tube 2000 to prevent the sample preservation solution 2004 from splashing out or being polluted by the outside environment after the pathogen adsorption portion 31 is placed in the sample collecting tube 2000 containing the sample preservation solution 2004.

According to an embodiment of the present disclosure, the filter layer has a fluffy state in which the filter layer is adapted to filter incoming air from the air vent, and a compressed state in which the filter layer is air-tight and water-impermeable.

In order to ensure that the wearer breathes smoothly and enables the filter layer to have better air permeability and filtering effect, the filter layer may be formed of a compressible loose material. In the sampling process, the filter layer is in the fluffy state and is adapted to filter the incoming air from the air vent, which avoids the viruses in the outside environment from polluting an adsorbent material and alleviates the stuffy feeling when the mask 1000 is worn. During the sampling, the filter layer may be compressed into a water-impermeable and air-tight sealing layer to prevent the sample preservation solution 2004 from splashing out. The filter layer in the present disclosure may realize flexible switching.

According to an embodiment of the present disclosure, the mask 1000 further includes a tightening apparatus connected to the filter layer and adapted to compress the filter layer and seal the air vent when the tightening apparatus is tightened up. The tightening apparatus may be a pulling string. The filter layer is compressed by lifting and pulling of the string to form the water-impermeable and air-tight sealing layer.

According to an embodiment of the present disclosure, a waterproof sheet is further disposed outside the filter layer. The waterproof sheet is optionally pressed tight on the valve cover to seal the air vent. The waterproof sheet may further enhance water resistance during the sampling and prevent the sample preservation solution 2004 from splashing out to achieve an effect of sealing the sample collecting tube 2000.

According to an embodiment of the present disclosure, the breather valve 2 is detachably mounted on the mask body 1. The valve casing 21 and the valve cover 23 included in the breather valve 2 both have a threaded structure, and may be connected and assembled by rotating.

According to an embodiment of the present disclosure, the breather valve 2 is optionally mounted on the sample collecting tube 2000 to seal an inlet of the sample collecting tube 2000.

The inlet of the sample collecting tube 2000 has a threaded structure disposed thereon, which may match the breather valve 2. The valve casing 21 with the pathogen adsorption portion 31 or the valve cover 23 with the pathogen adsorption portion 31 may be directly put into the sample collecting tube 2000 after being detached, and the inlet of the sample collecting tube 2000 may be in threaded fit with the valve casing 21 through or in threaded fit with the valve cover 23 to achieve sealing of the sample collecting tube 2000.

In some embodiments, the breather valve 2 is optionally in threaded fit with the mask body 1 or the sample collecting tube 2000. When the breather valve 2 is in threaded fit with the mask body 1, virus collection may be realized. When the breather valve 2 is in threaded fit with the sample collecting tube 2000, the sealing of the sample collecting tube 2000 may be realized.

According to an embodiment of the present disclosure, the mask body 1 has a base 4 disposed thereon. The breather valve 2 is detachably mounted on the base 4. The base 4 plays a supporting and fixing role, is connected to the mask body 1, and may prevent the pathogen adsorption portion 31 from detaching from the breather valve 2.

According to an embodiment of the present disclosure, after the breather valve 2 is detached from the mask body 1, the pathogen adsorption portion 31 is adapted to move away from the breather valve 2 under the action of an external force to be in contact with the sample preservation solution 2004.

After the viruses in the exhaled gas of the wearer is collected, the pathogen adsorption portion 31 carrying the viruses is required to be taken out in order to test the sample. In one of the methods, the pathogen adsorption portion 31 is still connected to the breather valve 2, but moves away from the breather valve 2 under the action of the external force, so that the pathogen adsorption portion 31 can contact the sample preservation solution 2004.

According to an embodiment of the present disclosure, after the breather valve 2 is detached from the mask body 1, the pathogen adsorption portion 31 is adapted to be removed from the breather valve 2 under the action of the external force to be in contact with the sample preservation solution 2004.

In another method, the pathogen adsorption portion 31 detaches from the breather valve 2 under the action of the external force, which enables the pathogen adsorption portion 31 to fall into the sample preservation solution 2004 and to be in contact with the sample preservation solution 2004.

According to an embodiment of the present disclosure, the sampling structure further includes a fixation frame 32. The pathogen adsorption portion 31 is disposed on the fixation frame 32 and is fixed by the fixation frame 32.

According to an embodiment of the present disclosure, the pathogen adsorption portion 31 is disposed on an inner end of the fixation frame 32. An outer end of the fixation frame 32 is disposed inside the breather valve 2. A part of the breather valve 2 directly facing the outer end of the fixation frame 32 is formed as an elastic region which, when stressed, deforms and pushes the fixation frame 32.

It should be noted that the outer end herein refers to an end away from the wearer, and the inner end refers to an end close to the wearer.

The pathogen adsorption portion 31 is disposed on the end of the fixation frame 32 close to the wearer in order to collect the viruses in the exhaled gas of the wearer. The end of the fixation frame 32 away from the wearer is fixed on the base 4 or the breather valve 2. The end of the fixation frame 32 away from the wearer has the elastic region. When the elastic region is pressed, the fixation frame 32 moves accordingly.

Figure 11:
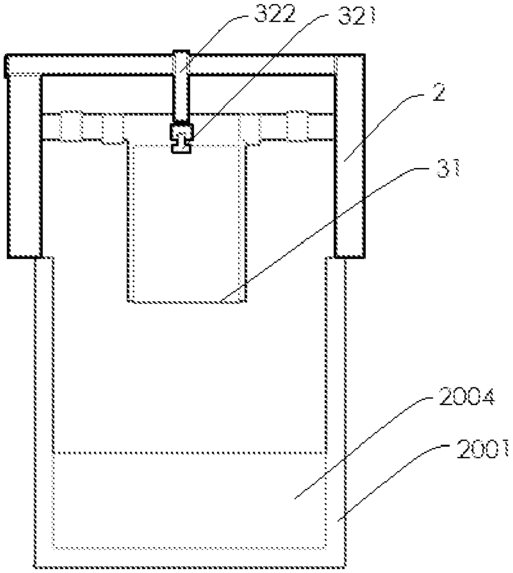
FIG. 11 is a first view of sampling according to yet another embodiment of the present disclosure.
Figure 12:
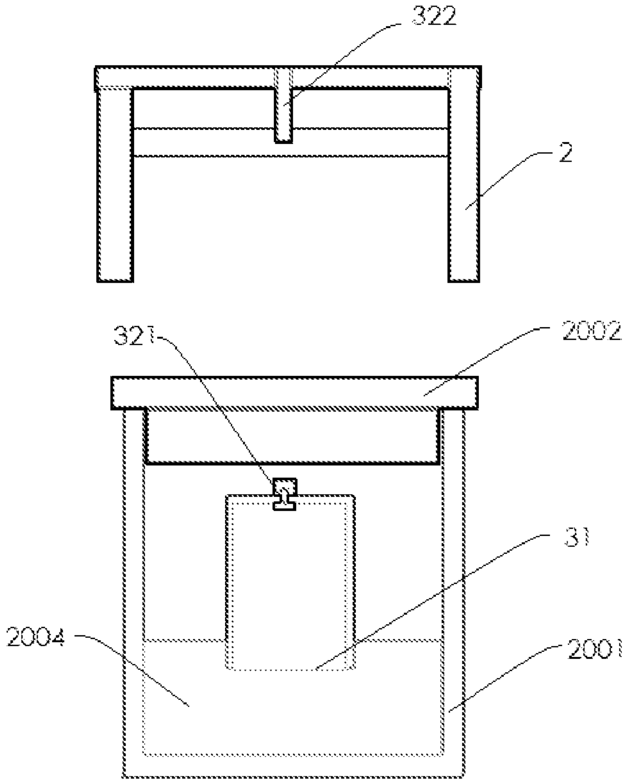
FIG. 12 is a second view of sampling according to yet another embodiment of the present disclosure.

According to an embodiment of the present disclosure, the pathogen adsorption portion 31 is disposed on the inner end of the fixation frame 32. The outer end of the fixation frame 32 extends beyond an outer side of the breather valve 2 to form a pressing portion. As illustrated in FIG. 11 to FIG. 12, the fixation frame 32 penetrates the breather valve 2, the pathogen adsorption portion 31 is disposed on the inner end of the fixation frame 32, and the outer end of the fixation frame 32 forms the pressing portion. The fixation frame 32 with the pathogen adsorption portion 31 moves downwards by applying a force to the pressing portion.

According to an embodiment of the present disclosure, the fixation frame 32 includes an inner fixation frame 321 and an outer fixation frame 322 that are separated from each other. The inner fixation frame 321 is connected to the breather valve 2 and is adapted to detach from the breather valve 2 under the action of an external force. The pathogen adsorption portion 31 is disposed on an inner end of the inner fixation frame 321. An outer end of the outer fixation frame 322 extends beyond the outer side of the breather valve 2 to form the pressing portion. An inner end of the outer fixation frame 322 optionally abuts against an outer end of the inner fixation frame 321.

Figure 2:
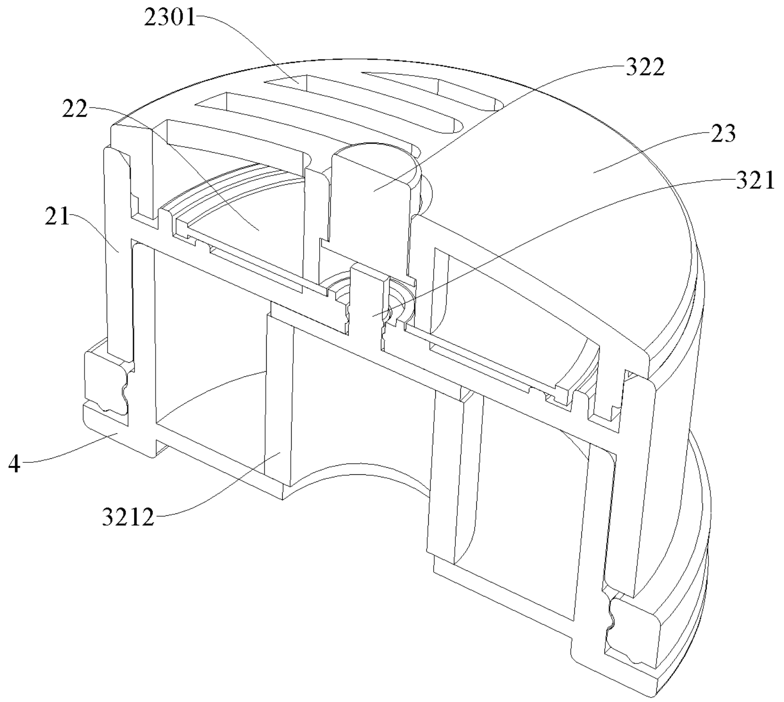
FIG. 2 is a cross-sectional view of a mask according to an embodiment of the present disclosure.
Figure 3:
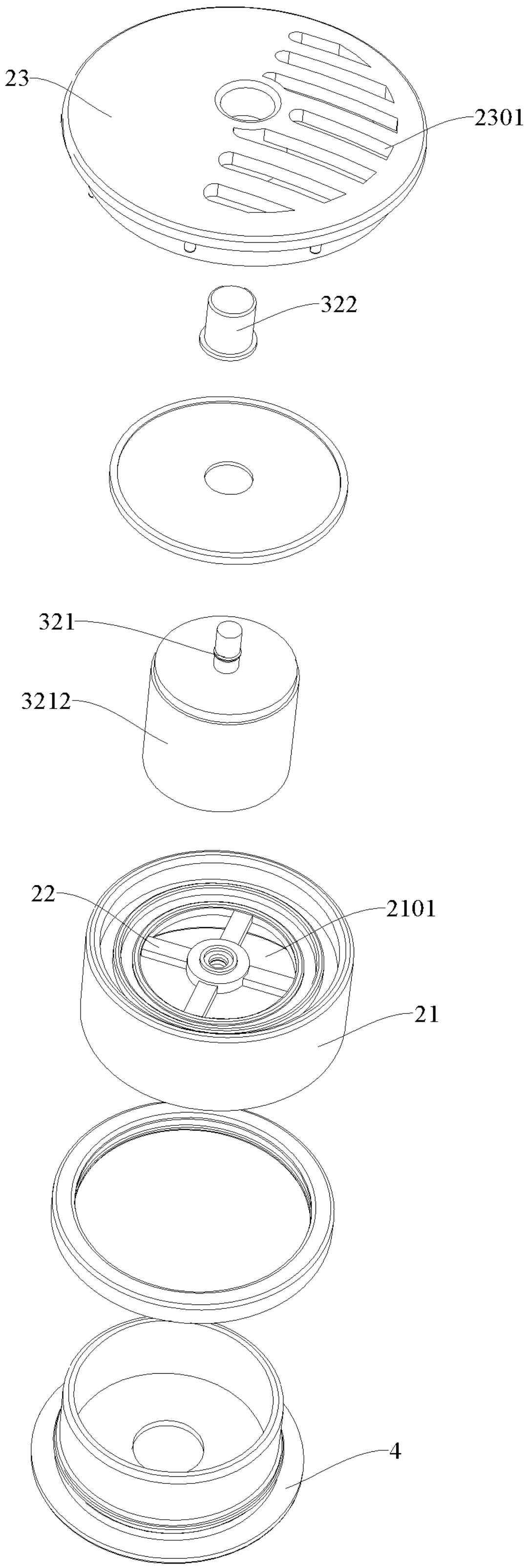
FIG. 3 is an exploded view of a mask according to an embodiment of the present disclosure.

As illustrated in FIG. 1 to FIG. 3, by applying a force to the outer fixation frame 322, the outer fixation frame 322 transmits the force to the inner fixation frame 321, which enables the fixation frame 32 with the pathogen adsorption portion 31 to move downwards until the pathogen adsorption portion 31 is disengaged from the breather valve 2. Therefore, the pathogen adsorption portion 31 may be aligned with the inlet of the sample collecting tube 2000 in such a manner that the pathogen adsorption portion 31 directly falls into the sample collecting tube 2000 containing the sample preservation solution 2004 after the pathogen adsorption portion 31 is disengaged from the breather valve 2, so as to complete the sampling.

According to an embodiment of the present disclosure, the breather valve 2 has a mounting hole. At least part of the inner fixation frame 321 passes through the mounting hole and is in interference fit with the mounting hole.

A part of the inner fixation frame 321 passing through the mounting hole is in interference fit with the mounting hole, which enables the inner fixation frame 321 to be stuck on the breather valve 2. After being pressed to apply the force, the inner fixation frame 321 moves downwards, which destroys a part of the inner fixation frame 321 that is in an interference fit with the mounting hole. At this time, the inner fixation frame 321 is in clearance fit with the mounting hole and may fall downwards freely.

It should be noted that the inner fixation frame 321 stuck on the breather valve 2 may be engaged with the mounting hole using a lower segment portion or a middle segment portion. A part, extending beyond the breather valve 2, of the outer end of the inner fixation frame 321 is long enough, which enables the part of the interference fit to completely detach from the mounting hole and enables the inner fixation frame 321 to fall smoothly and freely in a pressing process.

According to an embodiment of the present disclosure, a weak connection portion is disposed between the inner fixation frame 321 and the breather valve 2. The weak connection portion is adapted to be broken under the action of the external force to detach the inner fixation frame 321 from the breather valve 2.

Figure 9:
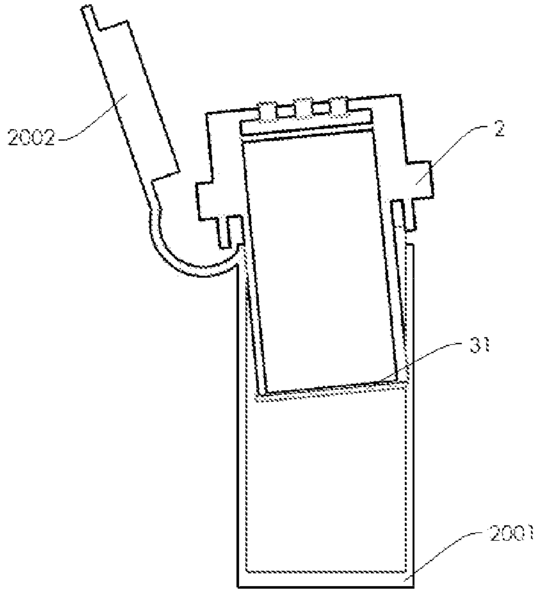
FIG. 9 is a first view of sampling according to another embodiment of the present disclosure.
Figure 10:
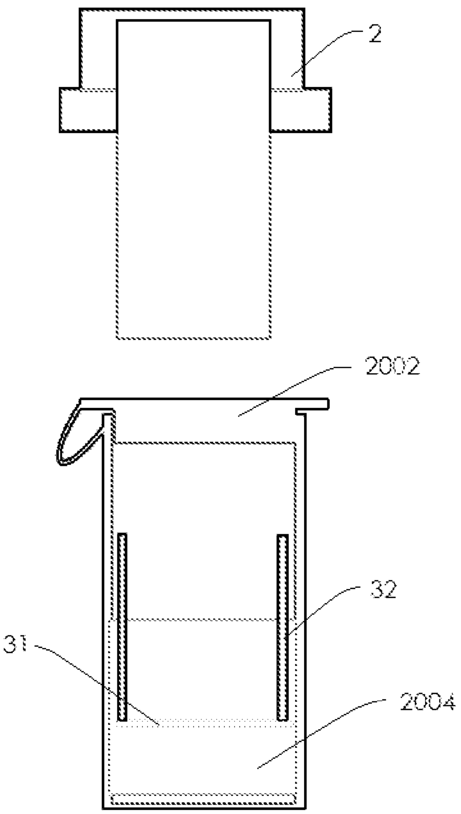
FIG. 10 is a second view of sampling according to another embodiment of the present disclosure.

As illustrated in FIG. 9 to FIG. 10, the sampling structure, the inner fixation frame 321, and the breather valve 2 detach from the mask body 1 together. The weak connection portion disposed between the inner fixation frame 321 and the breather valve 2 may be broken when a force is applied. When the sample is transferred to the sample collecting tube 2000, a force is applied to break the weak connection portion to enable the sampling structure to detach from the inner fixation frame 321 and the breather valve 2. Therefore, the sampling structure may be aligned with the inlet of the sample collecting tube 2000, and the sampling structure directly falls into the sample collecting tube 2000 containing the sample preservation solution 2004 after the sampling structure detaches from the inner fixation frame 321 and the breather valve 2, so as to complete the sampling.

According to an embodiment of the present disclosure, the breather valve 2 has a limiting portion disposed thereon. After the outer fixation frame 322 pushes the inner fixation frame 321 to detach from the breather valve 2, the limiting portion is adapted to restrict the outer fixation frame 322 from moving towards the inner fixation frame 321.

Since the outer fixation frame 322 is exposed in the air and is required to apply the force through a hand or other objects, in order to prevent the outer fixation frame 322 from passing through the mounting hole and falling into the sample collecting tube 2000 together with the inner fixation frame 321 to pollute the sample, in the present disclosure, the limiting portion is disposed on the breather valve 2 to prevent the outer fixation frame 322 from falling into the sample collecting tube 2000 together with the inner fixation frame 321.

According to an embodiment of the present disclosure, each of the inner fixation frame 321 and the outer fixation frame 322 is formed as a rod-shaped structure. The limiting portion includes a limiting block disposed on the outer fixation frame 322 and a limiting groove that is disposed on the breather valve 2 and in snap fit with the limiting portion. A diameter of the limiting portion is greater than a diameter of the inner fixation frame 321. The limiting groove matches the limiting block to prevent the outer fixation frame 322 from passing through the mounting hole to prevent the outer fixation frame 321 from falling into the sample collecting tube 2000 along with the inner fixation frame 321.

According to an embodiment of the present disclosure, the inner end of the fixation frame 32 has a supporting disk disposed thereon. The supporting disk has a first via hole. The pathogen adsorption portion 31 is disposed on the supporting disk and covers the first via hole.

A position where the pathogen adsorption portion 31 is mounted may be formed in a form of the supporting disk. A plurality of support feet may be disposed on the supporting disk. The pathogen adsorption portion 31 is mounted on upper surfaces or lower surfaces of the plurality of support feet in the supporting disk. The first via hole may be a gap between two support feet. The viruses in the exhaled gas of the wearer pass through the first via hole and are attached in the pathogen adsorption portion 31.

According to an embodiment of the present disclosure, an inner end of the fixation frame 32 has a supporting cylinder disposed thereon. An inner end of the supporting cylinder is opened. A cylinder wall of the supporting cylinder has a second via hole. The pathogen adsorption portion 31 is disposed on the supporting cylinder and covers the second via hole.

The position where the pathogen adsorption portion 31 is mounted may be formed in a form of the supporting cylinder. The second via hole on the supporting cylinder may be disposed on a wall surface of the supporting cylinder. The pathogen adsorption portion 31 is mounted on an inner wall surface or an outer wall surface of the supporting cylinder. The viruses in the exhaled gas of the wearer pass through the second via hole and are attached in the pathogen adsorption portion 31.

It should be emphasized that the inner end of the fixation frame 32 is changed to the supporting cylinder from the supporting disk. The pathogen adsorption portion 31 also changes from a sheet shape to a cylinder based on a difference in the fixation frame 32. When the pathogen adsorption portion 31 is formed in a form of the cylinder, a contact surface area is larger, which forms a structure that is similar to a filter tip and has higher efficiency of collecting the viruses compared with a sheet-shaped pathogen adsorption portion 31.

According to an embodiment of the present disclosure, the base 4 is formed as a cylindrical structure and has an air inlet hole in a bottom thereof. The pathogen adsorption portion 31 is adapted to block the air inlet hole. The air inlet hole allows the pathogen adsorption portion 31 to freely pass there through. The pathogen adsorption portion 31 can fall into the sample collecting tube 2000 from the air inlet hole.

According to an embodiment of the present disclosure, the inner end of the fixation frame 32 is disposed on the breather valve 2 or the base 4, and the pathogen adsorption portion 31 is disposed on the outer end of the fixation frame 32.

Figure 4:
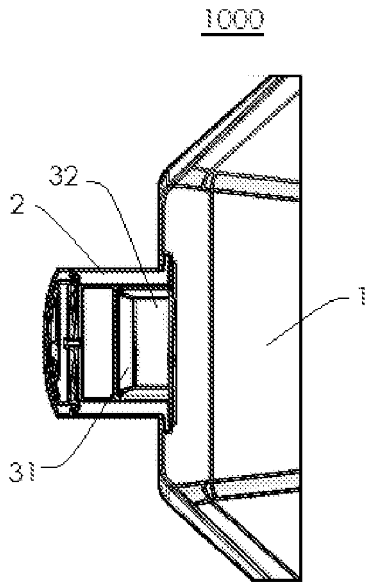
FIG. 4 is a schematic structural view of a mask according to another embodiment of the present disclosure.
Figure 5:
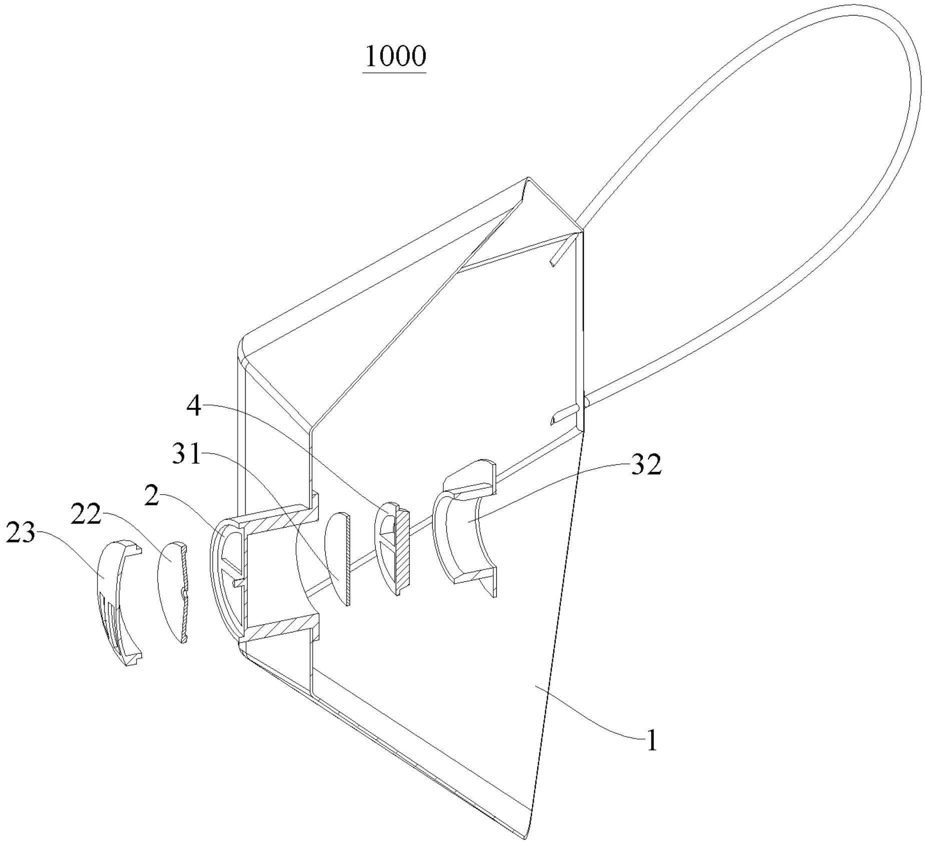
FIG. 5 is an exploded view of a mask according to another embodiment of the present disclosure.
Figure 6:
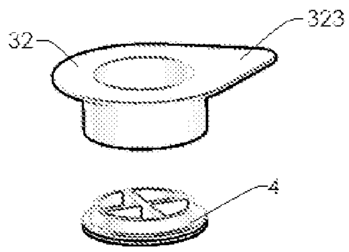
FIG. 6 is a view showing the engagement between a fixation frame and a base according to another embodiment of the present disclosure.
Figure 7:
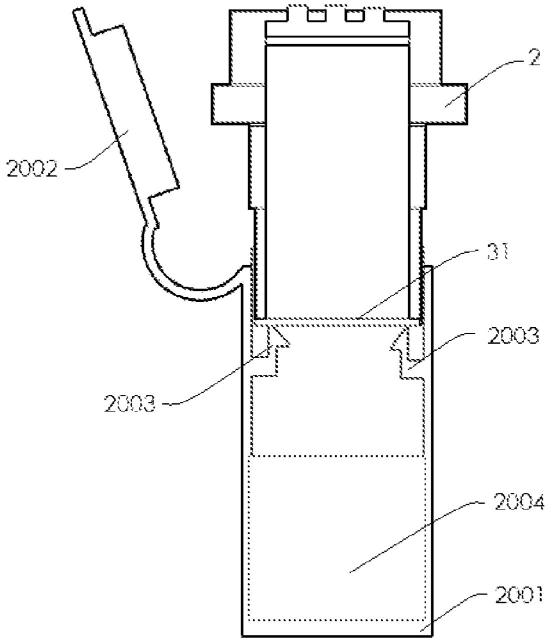
FIG. 7 is a first view of sampling according to an embodiment of the present disclosure.

As illustrated in FIG. 4 to FIG. 6, the inner end represents an end close to the wearer, and the outer end represents an end away from the wearer. The mask 1000 in an embodiment includes, from inside to outside, the mask body 1, the breather valve 2 or the base 4, the fixation frame 32, and the pathogen adsorption portion 31.

According to an embodiment of the present disclosure, the fixation frame 32 is formed as a fixation cylinder. An outer end of the fixation cylinder is opened. An inner end of the fixation cylinder has a third via hole. The pathogen adsorption portion 31 is disposed at the inner end of the fixation cylinder and covers the third via hole. The viruses in the exhaled gas of the wearer pass through the third via hole and are attached in the pathogen adsorption portion 31. An objective of the outer end of the fixation cylinder being opened is to enable the pathogen adsorption portion 31 to fall into the sample collecting tube 2000 after passing through the outer end of the fixation cylinder.

According to an embodiment of the present disclosure, the fixation cylinder is detachably disposed on the breather valve 2 or the base 4. In order to collect the sample, the fixation cylinder is required to be detached from the breather valve 2 or the base 4 first to facilitate a next sample collection operation.

In some embodiments, the fixation cylinder is snapped and fixed to the breather valve 2 or the base 4. When the sample is collected, the fixation cylinder is snapped and fixed on the breather valve 2 or the base 4. During the collection, the fixation cylinder is detached from the breather valve 2 or the base 4.

According to an embodiment of the present disclosure, the fixation cylinder has a pulling portion 323 disposed thereon. An objective of the pulling portion 323 is to give a collector a part that can be operated by hand. A predetermined distance exists between the pulling portion 323 and the pathogen adsorption portion 31. Therefore, on one hand, the risk of the sampling person being infected may be avoided, and on the other hand, the sample is protected from being polluted by viruses possibly existing on the hand.

According to an embodiment of the present disclosure, the fixation cylinder includes a fixation cylinder body and a bottom wall portion disposed at an outer end of the fixation cylinder body. The bottom wall portion has the third via hole. The bottom wall portion is configured to detach from the fixation cylinder body under the action of an external force. The pathogen adsorption portion 31 is mounted on the bottom wall portion. The sample collecting tube 2000 may be placed at a lower end of the bottom wall portion. Under the action of the external force, the bottom wall portion together with the pathogen adsorption portion passes through the third via hole and falls into the sample collecting tube 2000, so as to complete the sampling.

A specific process may be as follows: after the bottom wall portion with the pathogen adsorption portion 31 is removed from the mask body 1, the bottom wall portion with the pathogen adsorption portion 31 is detached from the fixation cylinder body. When the sample is transferred to the sample collecting tube 2000, the fixation cylinder body is in contact with the sample collecting tube 2000. The bottom wall portion of the pathogen adsorption portion 31 is pricked by force application of a cotton swab, which enables the bottom wall portion with the pathogen adsorption portion 31 to disengage from the fixation cylinder body, and the pathogen adsorption portion 31 to fall into the sample collecting tube 2000 with the sample preservation solution 2004, so as to complete the sampling.

According to an embodiment of the present disclosure, the bottom wall portion is detachably disposed on the fixation cylinder body. In some embodiments, the bottom wall portion is snapped and fixed to the fixation cylinder body. When the sample is collected, the bottom wall portion is snapped to and fixed on the fixation cylinder body. During the sampling, the bottom wall portion is detached from the fixation cylinder body.

According to an embodiment of the present disclosure, the breather valve 2 has an exhaust channel disposed therein. At least part of the sampling structure is disposed in the exhaust channel. The sampling structure may collect the viruses in the exhaled gas of the wearer in the exhaust channel.

According to an embodiment of the present disclosure, the pathogen adsorption portion 31 is disposed on an inner end of the fixation frame 32. An outer end of the fixation frame 32 is connected to the breather valve 2. At least part of the fixation frame 32 is adapted to be inserted into the sample collecting tube 2000 and is adapted to be broken off under the action of the external force.

Figure 8:
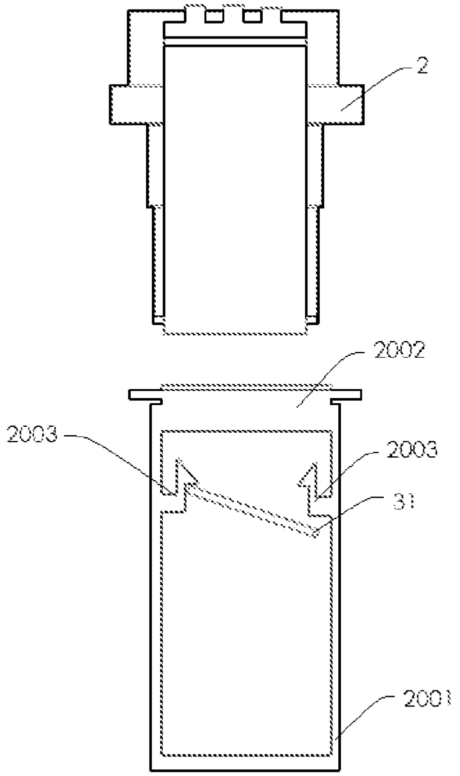
FIG. 8 is a second view of sampling according to an embodiment of the present disclosure.

As illustrated in FIG. 8 to FIG. 9, the pathogen adsorption portion 31 is mounted at the inner end of the fixation frame 32. The pathogen adsorption portion 31 detaches from the fixation frame 32 and falls off freely after the fixation frame 32 is broken off under the action of the external force.

According to an embodiment of the present disclosure, the fixation frame 32 has a strength weakened region configured to be broken under the action of the external force.

It should be noted that a structural type of the strength weakened region is not particularly limited, and may be selected by those of ordinary skill in the art based on actual needs. For example, in order to facilitate fracture of the fixation frame 32, a breakable score may be formed on the fixation frame 32, i.e., the strength weakened region. During the force application, stress of the strength weakening region is concentrated to reduce breaking difficulty. The strength weakened region may be formed as a region having a smaller cross section on the fixation frame 32, or may be formed as a region made of a material that is easy to break, which facilitates breaking under the action of the external force.

According to an embodiment of the present disclosure, the fixation frame 32 is formed as a cylindrical structure. An outer diameter of the fixation frame 32 is smaller than an inner diameter of the sample collecting tube 2000. In this way, the fixation frame 32 may be inserted into the sample collecting tube 2000. The external force is applied to enable the fixation frame 32 to be broken, which facilitates collection of the sample.

Specific operation is as follows: when the sample is transferred to the sample collecting tube 2000, after the fixation frame 32 together with the pathogen adsorption portion 31 is removed from the mask body 1, an end of the fixation frame 32 with the pathogen adsorption portion 31 is inserted into the sample collecting tube 2000, the fixation frame 32 partially abuts against a wall of the sample collecting tube 2000, an external force is applied to break the fixation frame 32, and the pathogen adsorption portion 31 falls into the sample collecting tube 2000 containing the sample preservation solution 2004, so as to complete the sampling.

According to an embodiment of the present disclosure, the pathogen adsorption portion 31 is disposed on an inner end of the fixation frame 32. An outer end of the fixation frame 32 is connected to the breather valve 2. The pathogen adsorption portion 31 is adapted to be cut by a cutting portion 2003 on the sample collecting tube 2000 to detach from the fixation frame 32.

During the sampling, the sample collecting tube 2000 is placed under the pathogen adsorption portion 31. After the fixation frame 32 and the pathogen adsorption portion 31 are removed from the mask body 1, the cutting portion 2003 on the sample collecting tube 2000 may cut the pathogen adsorption portion 31 off from the fixation frame 32, and the pathogen adsorption portion 31 directly falls into the sample collecting tube 2000 below to complete the sampling.

According to an embodiment of the present disclosure, the sampling structure further includes a limiting member 33, a mounting support foot 34, and a force bearing rod 35.

In some embodiments, the limiting member 33 is disposed on a valve body. A plurality of mounting support feet 34 is provided. An inner end of each of the plurality of mounting support feet 34 is connected to an outer periphery of the pathogen adsorption portion 31. An outer end of the force bearing rod 35 is formed as a force bearing end. An inner end of the force bearing rod 35 optionally applies a force towards the mounting support feet 34 or the pathogen adsorption portion 31 to deform the pathogen adsorption portion 31.

According to an embodiment of the present disclosure, an outer end of each of the mounting support feet 34 is hinged to the limiting member 33. The force bearing rod 35 is adapted to push the pathogen adsorption portion 31 to deform the pathogen adsorption portion 31.

Figure 13:
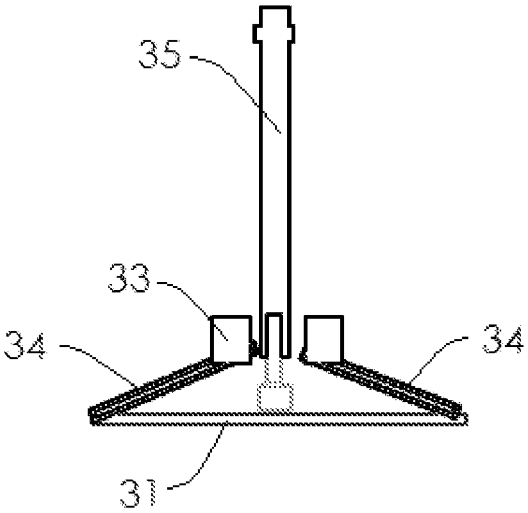
FIG. 13 is a first view of internal engagement of a sampling structure according to an embodiment of the present disclosure.
Figure 14:
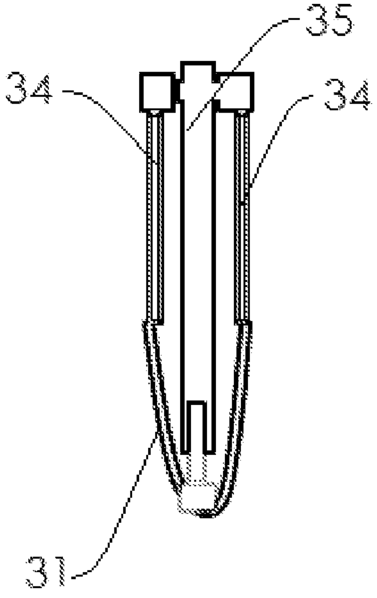
FIG. 14 is a second view of internal engagement of a sampling structure according to an embodiment of the present disclosure.

As illustrated in FIG. 13 to FIG. 14, during the sampling, the force bearing rod 35 is pushed inwards, the force bearing rod 35 applies the force to the pathogen adsorption portion 31, the pathogen adsorption portion 31 bulges inwards to deform, and then the deformed pathogen adsorption portion 31 is placed into the sample collecting tube 2000 containing the sample preservation solution 2004, so as to complete the sampling.

According to an embodiment of the present disclosure, an outer end of each of the mounting support feet 34 is connected to an inner end of the force bearing rod 35. The force bearing rod 35 is adapted to pull the outer end of each of the mounting support feet 34 to enable the mounting support feet 34 to be gathered up under pushing of the limiting member 33 and to deform the pathogen adsorption portion 31.

Figure 15:
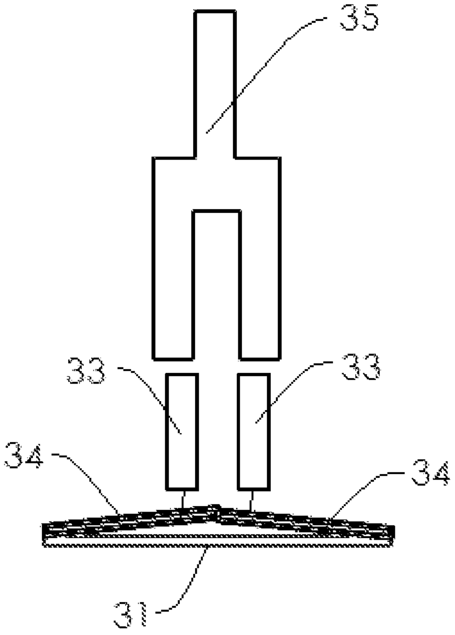
FIG. 15 is a first view of internal engagement of a sampling structure according to another embodiment of the present disclosure.
Figure 16:
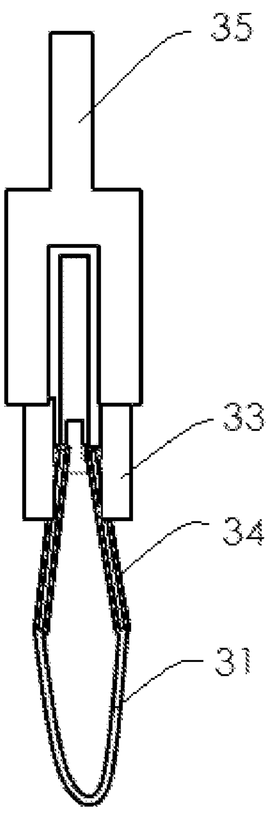
FIG. 16 is a second view of internal engagement of a sampling structure according to another embodiment of the present disclosure.

As illustrated in FIG. 15 to FIG. 16, during the sampling, the force bearing rod 35 is pulled outwards, and the outer ends of the mounting support feet 34 move outwards along with the force bearing rod 35. The limiting member 33 limits a distance over which the mounting support feet 34 move outwards. Since there is a gap between limiting members 33, a part of the mounting support feet 34 after passing through the gap is gathered up under the pushing of the limiting member 33, the pathogen adsorption portion 31 bulges inwards to deform, and then the deformed pathogen adsorption portion 31 is placed into the sample collecting tube 2000 containing the sample preservation solution 2004, so as to complete the sampling.

According to an embodiment of the present disclosure, the limiting member 33 is formed as an annular limiting ring, and there is a gap between limiting rings, which may restrict the mounting support feet 34 from moving outwards, and meanwhile, may achieve the function of gathering up the mounting support feet 34.

According to an embodiment of the present disclosure, the pathogen adsorption portion 31 is connected to the fixation frame 32 through a water-soluble material layer.

During the sampling, the pathogen adsorption portion 31 and the fixation frame 32 may be sealed together in the sample preservation solution 2004. Since the sample preservation solution 2004 is mostly a water-based preservation solution, the water-soluble material layer of the pathogen adsorption portion 31 may be dissolved in the sample preservation solution 2004 by shaking the sample collecting tube 2000, and thus the pathogen adsorption portion 31 detaches from the fixation frame 32, which further simplifies the sampling operation and significantly shortens sampling time.

According to the present disclosure, the sample collecting tube 2000 includes a collecting tube body 2001 and a cover body 2002.

In some embodiments, the collecting tube body 2001 has an opening and a sample collecting solution disposed inside. The cover body 2002 is detachably disposed on the collecting tube body 2001 to close or expose the opening. The sample collecting tube 2000 body has a cutting portion 2003 disposed therein, and the cutting portion 2003 is adapted to cut the pathogen adsorption portion 31.

Since the valve casing 21 has the threaded structure, the valve casing 21 may be directly engaged with the threaded structure on the collecting tube body 2001 to replace the cover body 2002 to seal the opening on the collecting tube body 2001, and the pathogen adsorption portion 31 on the valve casing 21 may be cut by the cutting portion 2003 in the sample collecting tube 2000 body, and therefore detaches from the valve casing 21. There is no need to excessively contact the pathogen adsorption portion 31, which reduces the risk of the collector being infected.

According to an embodiment of the present disclosure, the cutting portion 2003 is disposed on an inner peripheral wall of the collecting tube body 2001. In general, the cover body 2002 is partially plugged into the collecting tube body 2001 to seal the collecting tube body 2001. Therefore, the cutting portion 2003 is disposed on the inner peripheral wall of the collecting tube body 2001 to facilitate separating of the pathogen adsorption portion 31 on the valve casing 21.

According to an embodiment of the present disclosure, the cutting portion 2003 is disposed adjacent to the opening. The sample preservation solution 2004 is stored at the bottom of the collecting tube body 2001. In order not to pollute the sample preservation solution 2004 and to ensure the accuracy of the result, the cutting portion 2003 is disposed adjacent to the opening and is away from the sample preservation solution 2004, and only the pathogen adsorption portion 31 falls into the sample preservation solution 2004 after being cut, which is beneficial to the accuracy of the sample result.

According to an embodiment of the present disclosure, a plurality of cutting portions 2003 is provided. The plurality of cutting portions 2003 is arranged at intervals in a circumferential direction of the collecting tube body 2001. The plurality of cutting portions 2003 facilitates separating of the pathogen adsorption portion 31 on the valve casing 21.

According to the present disclosure, a pathogen collecting apparatus includes a sample collecting tube 2000 and the mask 1000 described above.

In some embodiments, the sample collecting tube 2000 has a sample preservation solution 2004 disposed therein. The pathogen adsorption portion 31 on the mask 1000 is adapted to enter the sample collecting tube 2000 to be in contact with the sample preservation solution 2004 in the sample collecting tube 2000.

In the description of the present disclosure, it is to be understood that the term such as "inner", "outer", "circumferential", etc., is based on the orientation or position relationship shown in the drawings, and is only for the convenience of describing the present disclosure and simplifying the description, rather than indicating or implying that the associated device or element must have a specific orientation, or be constructed and operated in a specific orientation, and therefore cannot be understood as a limitation on the present disclosure.

In the description of the present disclosure, "a plurality of" means at least two.

In the description of this specification, descriptions with reference to the terms "an embodiment", "some embodiments", "exemplary embodiments", "examples", "specific examples", or "some examples" etc., mean that specific features, structure, materials or characteristics described in conjunction with the embodiment or example are included in at least one embodiment or example of the present disclosure. In this specification, the schematic representations of the above terms do not necessarily refer to the same embodiment or example. Moreover, the described specific features, structures, materials or characteristics may be combined in any one or more embodiments or examples in a suitable manner.

Although embodiments of the present disclosure have been illustrated and described, it is conceivable for those of ordinary skill in the art that various changes, modifications, replacements, and variations can be made to these embodiments without departing from the principles and ideas of the present disclosure. The scope of the present disclosure shall be defined by the claims as appended and their equivalents.

What is claimed is:

1. A mask, comprising:

a mask body;

a breather valve fixed on the mask body; and a sampling structure comprising a pathogen adsorption portion, wherein the pathogen adsorption portion is disposed on an inner side of the breather valve and is adapted to adsorb pathogens in exhaled gas, and wherein the pathogen adsorption portion is adapted to enter a sample collecting tube to be in contact with a sample preservation solution in the sample collecting tube, wherein the breather valve comprises:

a valve casing having an exhaust vent;

a valve plate disposed on the valve casing and configured to expose the exhaust vent when the wearer exhales and to close the exhaust vent when the wearer inhales; and a valve cover arranged on an outer side of the valve casing, and an exhaust space being defined by the valve cover and the valve casing;

wherein the valve cover has an air vent in communication with the exhaust space, wherein the valve plate is disposed in the exhaust space, and wherein the valve plate has a filter layer disposed on an outer side thereof, the filter layer having a fluffy state in which the filter layer is adapted to filter incoming air from the air vent, and a compressed state in which the filter layer is air-tight and water-impermeable.

2. The mask according to claim 1, wherein the breather valve is a one-way valve and is configured to be opened when a wearer exhales and to be closed when the wearer inhales.

3. The mask according to claim 1, wherein the pathogen adsorption portion is disposed on an inner side of the exhaust vent.

4. The mask according to claim 1, wherein one end of the valve plate is disposed on the valve casing, and another end of the valve plate is pressed tight on the valve casing to expose or close the exhaust vent.

5. The mask according to claim 4, wherein a plurality of exhaust vents is provided, wherein the plurality of exhaust vents is arranged at intervals in a circumferential direction of the valve casing; and wherein the valve plate is formed in an annular shape, wherein an inner end of the valve plate is fixedly connected to the valve casing, and an outer end of the valve plate is pressed tight on the valve casing to expose or close the plurality of exhaust vents.

6. The mask according to claim 1, wherein the valve plate has a plurality of micropores, the plurality of micropores being configured to:

when the wearer exhales, become larger in pore diameter and be in communication with the exhaust vent; and when the wearer inhales, become smaller in the pore diameter until the plurality of micropores is closed.

7. The mask according to claim 1, wherein the valve casing is detachably disposed on the mask body.

8. The mask according to claim 7, wherein the valve casing is in threaded fit with the mask body.

9. The mask according to claim 7, wherein the valve casing is connected to the pathogen adsorption portion.

10. The mask according to claim 1, wherein a blocking cover that optionally seals the air vent is disposed on the valve cover.

11. The mask according to claim 1, wherein the valve cover is detachably connected to the valve casing.

12. The mask according to claim 11, wherein the valve cover is in threaded fit with the valve casing.

13. The mask according to claim 11, wherein the valve cover is connected to the pathogen adsorption portion.

14. The mask according to claim 1, further comprising:

a tightening apparatus connected to the filter layer and adapted to compress the filter layer and seal the air vent when the tightening apparatus is tightened.

15. The mask according to claim 1, wherein a waterproof sheet is disposed outside the filter layer, the waterproof sheet being pressed tight on the valve cover to seal the air vent.

16. A pathogen collecting apparatus, comprising:

a sample collecting tube having a sample preservation solution disposed therein; and the mask according to claim 1.

* * * * *